March 19, 1974 W. A. WARRINER Plant Pat. 3,522
ROSE PLANT
Filed Nov. 28, 1972
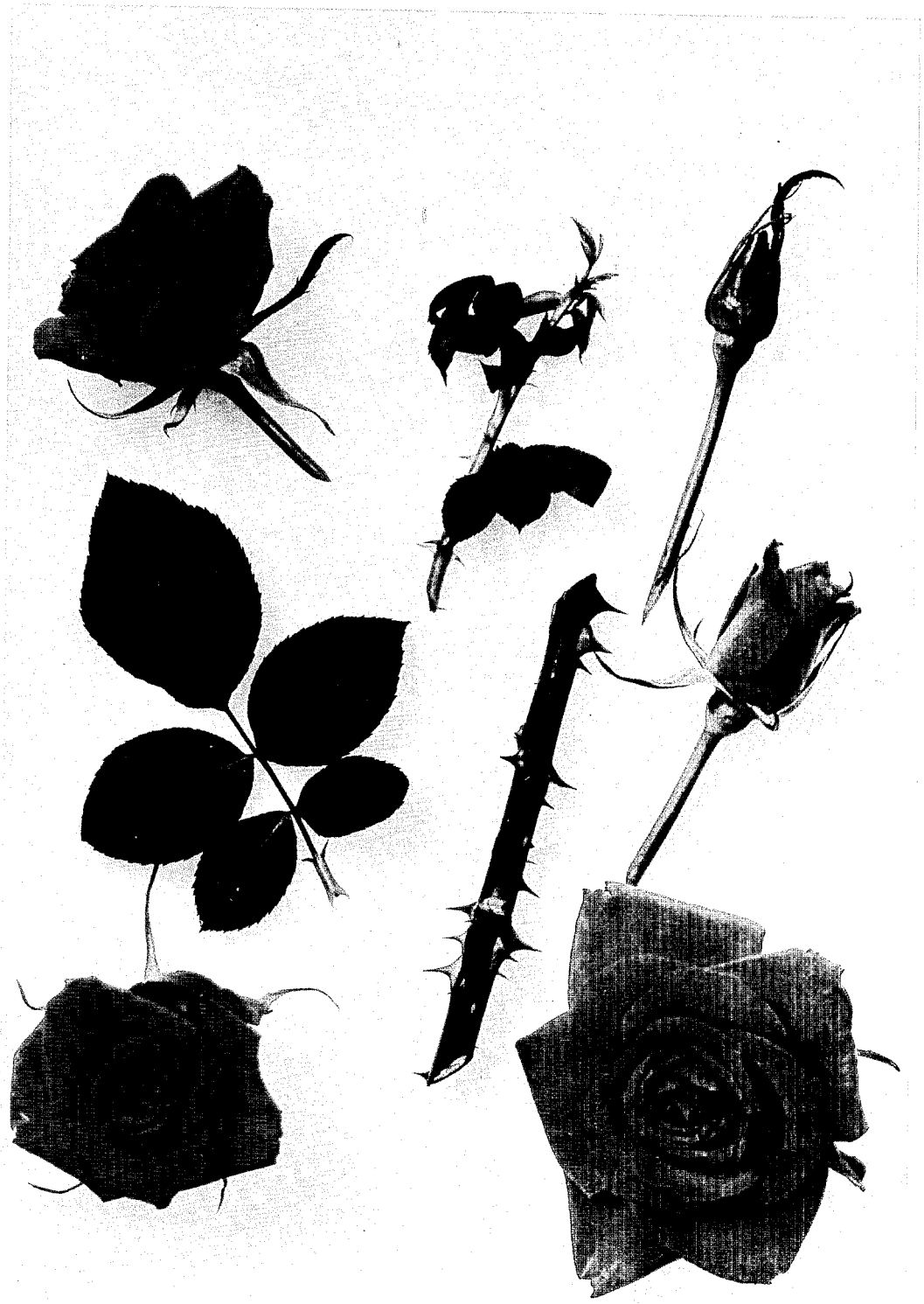

United States Patent Office

Plant Pat. 3,522

Patented Mar. 19, 1974

3,522

ROSE PLANT

William A. Warriner, Tustin, Calif., assignor to Jackson & Perkins Company, Medford, Oreg.

Filed Nov. 28, 1972, Ser. No. 310,030

Int. Cl. A01h *5/00*

U.S. Cl. Plt.—20 1 Claim

The present invention relates to a new and distinct variety of rose plant of the hybrid tea class which was originated by me by crossing an unnamed seedling variety with pollen from the variety Forever Yours, U.S. Pl. Pat. 2,443.

The primary objective of this breeding was to produce a new rose variety of vigorous character, with red, nonfading or nonblueing flower color, suitable for greenhouse production of cut flowers. This objective was substantially achieved along with other desirable improvements over older varieties, as evidenced by the following unique combinations of characteristics which are outstanding in the new variety and which distinguish it from its parents as well as from all other varieties of which I am aware:

(1) A very vigorous, upright, slightly angular habit of growth.
(2) A tendency for the top several leaves to contain only 3 leaflets per leaf.
(3) Leaves are generally smaller and darker green than its pollen parent, Forever Yours.
(4) Bud and flower color are a slightly lighter shade of red than Forever Yours, and after several days as a cut flower the pigment of this new variety retains more nearly its opening color than Forever Yours, showing little tendency to turn toward Magenta.
(5) Little or no fragrance.
(6) A high degree of resistance to rose powdery mildew.

Asexual reproduction of this new variety by budding, as performed at Wasco, California, proves that the foregoing characteristics and distinctions reproduce truly and are established and transmitted through succeeding propagations.

The accompanying drawing shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling
- *Seed parent.*—Unnamed seedling.
- *Pollen parent.*—Forever Yours (U.S. Pl. Pt. 2,443).

Classification:
- *Botanic.*—*Rosa hybrid.*
- *Commercial.*—Hybrid tea.

FLOWER

Observations were made at Irvine, Calif., in mid-October of flowers from greenhouse grown plants.

Blooming habit: Recurrent—continuous.

Bud:
- *Form.*—Long, pointed, ovoid.
- *Color.*—When sepals first divide: Currant Red (821). When half blown: inside of petals, Currant Red (821/1); reverse of petals, Currant Red (821/1).
- *Sepals.*—Color: Outer surface—Scheeles Green (860/1). Inner surface—Scheeles Green (860/1), covered with white tomentum. Three appendaged sepals lightly appendaged. Two unappendaged sepals hairy edged.
- *Receptacle.*—Color: Near Scheeles Green (860/3). Shape: Funnel. Size: Large. Surface: Smooth.
- *Peduncle.*—Length: Short. Surface: Prickly. Color: Scheeles Green (860/3). Strength: Stiff, erect.
- *Opening.*—In early stages, petals curl back slightly—show very little curling when fully open.

Bloom:
- *Size.*—Large. Average size when fully expanded, 4 to 4½ inches.
- *Borne.*—Singly.
- *Stems.*—Long, strong.
- *Form.*—When first open, high center. Permanence—Retains its form until the end.
- *Petalage.*—Number of petals under normal conditions 27–35.
- *Color.*—Center of flower: Upper side of petals close to Currant Red (821/2) but slightly more Maenta. When compared to petals of Forever Yours from the same greenhouse, these petals are much lighter. Reverse side of petals lighter than Cardinal Red (822/3). Other petals: Upper side of petals, Cardinal Red (822/3). Reverse of petals Cardinal Red (822/3). Base of petals very small white areas. General tonality from a distance near Currant Red (821/2). No variegations.
- *Discoloration.*—General tonality at end of first day same as full open. By third day very little change.
- *Fragrance.*—None.

Petals:
- *Texture.*—Thick.
- *Surface.*—Inside—velvety. Reverse—satiny.
- *Shape.*—Round.
- *Form.*—Tips slightly recurved.
- *Arrangement.*—Imbricated.
- *Petaloids in center.*—Few.
- *Persistence.*—Drop off cleanly.
- *Lastingness.*—On the plant—very long. As cut flower—very long; seven to eight days in room temperature after conditioning in 40° for one day.

Reproductive parts:
- *Stamens, anthers.*—Large. Color—Rhodamine Pink (527) in midrib area, Chrome Yellow (605) border area. Arrangement—regular around styles.
- *Stamens, filaments (threads).*—Long. Color—near Solferino Purple (26).
- *Pollen.*—Chrome Yellow (605).
- *Styles.*—Loosely separated, of uneven lengths. Color—Solferino Purple (26).
- *Stigmas.*—Color—white.
- *Ovaries.*—All enclosed in calyx.

PLANT

Form: Bush.

Growth: Very vigorous, upright.

Foliage: Number of leaflets on normal midstem leaves—5. Stems often have 3 leaflet leaves at upper 4 or 5 nodes.
- *Size.*—Large.
- *Quantity.*—Normal.
- *Color.*—New foliage: Lighter than Fern Green (0862/3) overlaid with a color of similar hue but lighter density than Oxblood Red (00823/3). Lower side of new foliage predominantly a lighter tint of Oxblood Red (00823/3). Old foliage: Darker than Spinach Green (0960).

Leaflets:
- *Shape.*—Oval pointed.
- *Texture.*—Upperside leathery. Under side smooth. Ribs and veins ordinary.

*Edge.*—Serrated.
*Serration.*—Single, small.
*Petiole*—(rachis).—Color—reddish. Underside—Prickles and a few thorns.
*Stipules.*—Long, serrated.
*Disease Resistance.*—Very resistant to mildew under normal growing conditions at Irvine, Calif.

Wood:
*New Wood.*—Color—light green. Bark—smooth.
*Old Wood.*—Color—green. Bark—smooth.

Prickles:
*Quantity.*—On main stalks—many. On laterals—ordinary.
*Form.*—Broad base, hooked downward.
*Color.*—When young—green.
*Position.*—Irregular.

Small prickles:
*Quantity.*—On main stalks—few. On laterals—few.
*Color.*—Green.

I claim:

1. A new and distinct variety of rose plant of the hybrid tea class, substantially as herein shown and described, characterized particularly as to novelty by the unique combination of its vigorous growth, suitability as a greenhouse cut flower variety, nonfading and nonblueing Currant Red flower color, its characteristic three leaflet leaves on the upper several nodes, and its relatively high degree of resistance to rose powdery mildew.

No references cited.

ROBERT E. BAGWILL, Primary Examiner

PO-1050
(5/69)

UNITED STATES PATENT OFFICE
CERTIFICATE OF CORRECTION

Patent No. Plant 3,522 Dated March 19, 1974

Inventor(s) WILLIAM A. WARRINER

It is certified that error appears in the above-identified patent and that said Letters Patent are hereby corrected as shown below:

Column 2, lines 19 and 20, "Ma-enta" should read --Magenta--.
Column 2, line 23, "Other" should read --outer--.

Signed and sealed this 24th day of September 1974.

(SEAL)
Attest:

McCOY M. GIBSON JR.
Attesting Officer

C. MARSHALL DANN
Commissioner of Patents